United States Patent [19]
Voss et al.

[11] Patent Number: 5,426,300
[45] Date of Patent: Jun. 20, 1995

[54] PORTABLE GCMS SYSTEM USING GETTER PUMP

[75] Inventors: Gunter Voss, Much, Germany; Stephan J. DeLuca, Syracuse; Gregory Adams, Jamesville, both of N.Y.

[73] Assignee: Leybold Inficon, Inc., E. Syracuse, N.Y.

[21] Appl. No.: 123,755

[22] Filed: Sep. 17, 1993

[51] Int. Cl.[6] .................. H01J 49/04; H01J 49/24
[52] U.S. Cl. ................................ 250/288; 250/289
[58] Field of Search .................. 250/288, 288 A, 289

[56] References Cited

U.S. PATENT DOCUMENTS

| | | | |
|---|---|---|---|
| 2,060,861 | 11/1936 | Glans | 417/48 |
| 2,511,726 | 6/1950 | Lockwood | 96/147 |
| 3,197,945 | 8/1965 | Zaphiropoulos | 417/48 |
| 3,208,203 | 9/1965 | Markevitch | 96/147 |
| 3,310,227 | 3/1967 | Milleron | 230/101 |
| 3,638,401 | 2/1972 | Kabler | 55/158 |
| 3,791,106 | 2/1974 | Haley | 55/158 |
| 3,868,239 | 2/1975 | Visser | 96/152 |
| 3,942,546 | 3/1976 | Radd | 137/93 |
| 3,953,755 | 4/1976 | Kuus et al. | 313/174 |
| 3,992,626 | 11/1976 | Bursack | 250/288 |
| 4,127,790 | 11/1978 | Kuus et al. | 313/174 |
| 4,146,277 | 3/1979 | Santoro | 96/134 |
| 4,193,398 | 3/1980 | Refson | 417/48 |
| 4,272,259 | 6/1981 | Patterson | 417/48 |
| 4,481,441 | 11/1984 | Vangils | 313/481 |
| 4,888,295 | 12/1989 | Zaromb et al. | 436/161 |
| 4,907,948 | 3/1990 | Barosi | 417/53 |
| 5,105,652 | 4/1992 | Manfredi et al. | 73/23.25 |
| 5,149,429 | 9/1992 | Baker | 96/134 |
| 5,191,980 | 3/1993 | Boffito | 417/48 |

FOREIGN PATENT DOCUMENTS 3332647 3/1985 Germany .................. 417/51
2249662 6/1990 United Kingdom .

Primary Examiner—Jack I. Berman
Attorney, Agent, or Firm—Harris Beach & Wilcox

[57] ABSTRACT

A gas analyzing system that includes a vacuum chamber containing a mass spectrometer and a sampling device for introducing a gas sample into the chamber. A sorption pump is operatively connected to the chamber which is capable of maintaining the chamber at a high vacuum. The pump includes a diffusion barrier that provides smooth pumping characteristics and repeatable short term system behavior when sample pulses are introduced into the system.

21 Claims, 5 Drawing Sheets

PORTABLE GCMS SYSTEM USING GETTER PUMP

BACKGROUND OF THE INVENTION

This invention relates generally to a mass spectrometer utilizing an improved sorption pump for maintaining the vessel containing the mass spectrometer at a high vacuum. More specifically, the invention relates to a portable analytical module that includes a mass spectrometer and an improved sorption pump that is removably connected to a service module.

For the most part, sorption pumps cannot maintain the high vacuum pressure required in many analytical process applications and exhibit erratic pumping characteristics both in terms of short term and long term usage. The pumping speed generally falls off rather rapidly as the sorptive materials absorb active gas. Similarly, the ability of the pump to adapt to rapid changes in sample composition is extremely poor. Furthermore, sorption pumps in present use cannot be regenerated in situ and thus, must be changed on a regular basis. Safe handling of the sometimes hazardous sorptive materials during changeover can also pose problems.

In United Kingdom application 2,249,662 there is described a portable mass spectrometer system that includes a gas chromatograph and a mass analyzer housed within a vacuum chamber. A high vacuum ion pump is also housed within the portable system. The pump consumes a good deal of the total electrical energy available and places a heavy load on the system's batteries and restricts the amount of time that is available for sampling in the field.

SUMMARY OF THE INVENTION

It is therefore an object of the invention to improve mass spectrometry.

A further object of the invention is to improve mass spectrometry through utilization of a sorption pump having a substantial constant pumping speed over the life of the sorptive material.

A still further object of the present invention is to provide a portable mass spectrometer that utilizes a sorption pump to maintain the vacuum chamber housing the instrument at a high vacuum pressure.

Another object of the present invention is to smooth the pumping characteristics of a sorption pump used to maintain a mass spectrometer in a high vacuum.

Yet another object of the present invention is to provide a sorption pump for use in conjunction with a mass spectrometer that exhibits repeatable short term behavior in response to rapid changes in gas composition.

Still another object of the present invention is to provide a portable mass spectrometer utilizing a sorption pump for maintaining the vacuum vessel housing the instrument at a high vacuum that can be regenerated in situ.

These and other objects of the present invention are attained by means of a mass spectrometer that is housed in a vacuum chamber and a sorption pump connected to the chamber for holding the chamber at a high vacuum. The sorption pump contains a non-evaporable getter material which is shielded from the chamber by a diffusion barrier so that gas contained in the chamber requires some finite period of time to cross the barrier and reach the material. The barrier functions to smooth out the pumping characteristics of the sorption pump and also provides for a repeatable short term system response when reacting to fast changes in the composition of the gas being analyzed.

In the main embodiment of the invention the mass spectrometer and sorption pump are housed within a portable module that is connected to a service module.

BRIEF DESCRIPTION OF THE DRAWINGS

For a better understanding of these and other objects of the present invention, reference shall be made to the following detailed description of the invention which is to be read in association with the accompanying drawings, wherein.

DETAILED DESCRIPTION OF A PREFERRED EMBODIMENT

Figure 1:
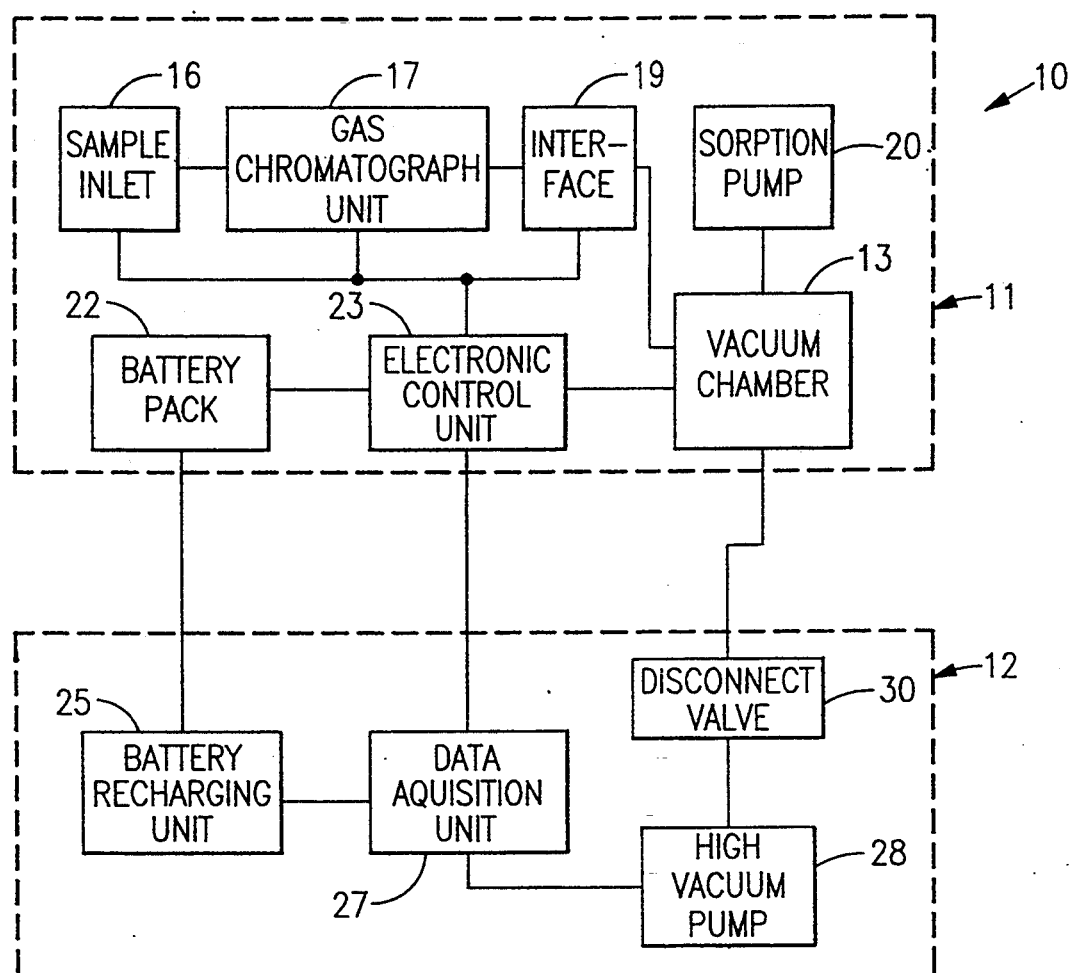
FIG. 1 is a block diagram of an analyzing system, including a portable analytical module and a service module, embodying the teachings of the present invention.

Turning initially to FIG. 1, there is illustrated a block diagram outlining the component parts of a gas analyzing system 10 embodying the teachings of the present invention. The system involves a portable analytical module 11 that is removably attached to a service module 12. When detached from the service module, the analytical module becomes self-sustaining and can be carried conveniently in the field to acquire gas samples and related data from remote locations. The data may be processed and displayed on site or stored in memory and later delivered to an external computer for further processing.

Figure 3:
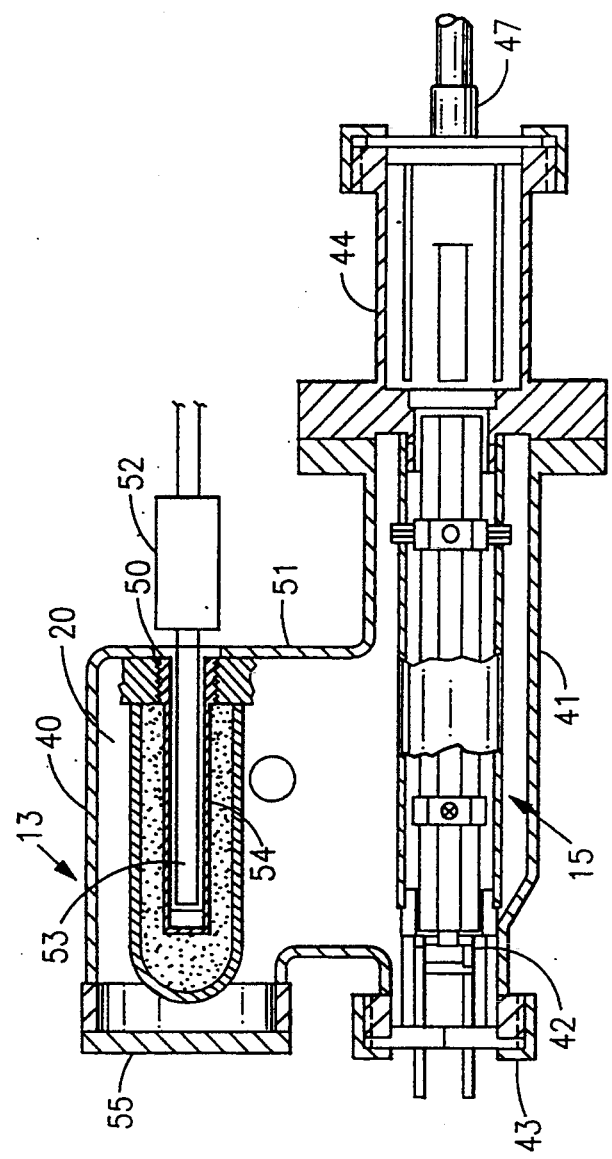
FIG. 3 is a side elevation, in section, illustrating the mass spectrometer employed in the portable analytical module.

The analytical module includes a vacuum chamber 13 housing a mass spectrometer 15 (FIG.3). The mass spectrometer may be a quadrupole, ion trap, time of flight, ion cyclotron, or magnetic sector type that is capable of isolating and analyzing various sample components brought into the vacuum chamber by a carrier gas. The sample to be analyzed is initially captured at the sample inlet 16 and delivered to a gas chromatograph unit 17 that contains a column for separating the gas components in a well known manner. The output of the gas chromatograph unit is connected to the vacuum chamber 13 by means of a gas chromatograph mass spectrometer interface 19. Preferably the interface is a membrane separator which does not require a separate pumping system. Other interfaces known and used in the art, such as jet separators, direct gas coupling and the like may also be used without departing from the teachings of the present invention.

A sorption pump 20, which will be explained in greater detail below, is connected to the vacuum chamber 13 and serves to maintain the chamber at a high vacuum, preferably equal to or greater than $10^{-5}$ torr.

The analytical module also includes a rechargeable battery pack 22 and an electronic control unit 23 that provides power to the various system components. The control unit contains a micro-processor for controlling the operation of the various module components and for analyzing sample data as well as a memory section for storing data from the mass spectrometer.

The service module 12 minimally contains a battery recharging unit 25 that is connectable to the battery pack 22 in the analytical module for recharging the battery pack when the two modules are attached. A data acquisition unit 27 is contained in the service module to accept data from the control unit 23. A high vacuum pump 28 in the service module is connectable to the vacuum chamber 13 in the analytical module through means of a disconnect valve 30. The high vacuum pump serves to pump the vacuum chamber down to the desired operating level which is then maintained by the sorption pump when the analytical module is separated from the service module. The high vacuum pump may be a diffusion pump, a turbo-molecular pump or any other suitable pump known and used in the art for similar purposes.

Figure 2:
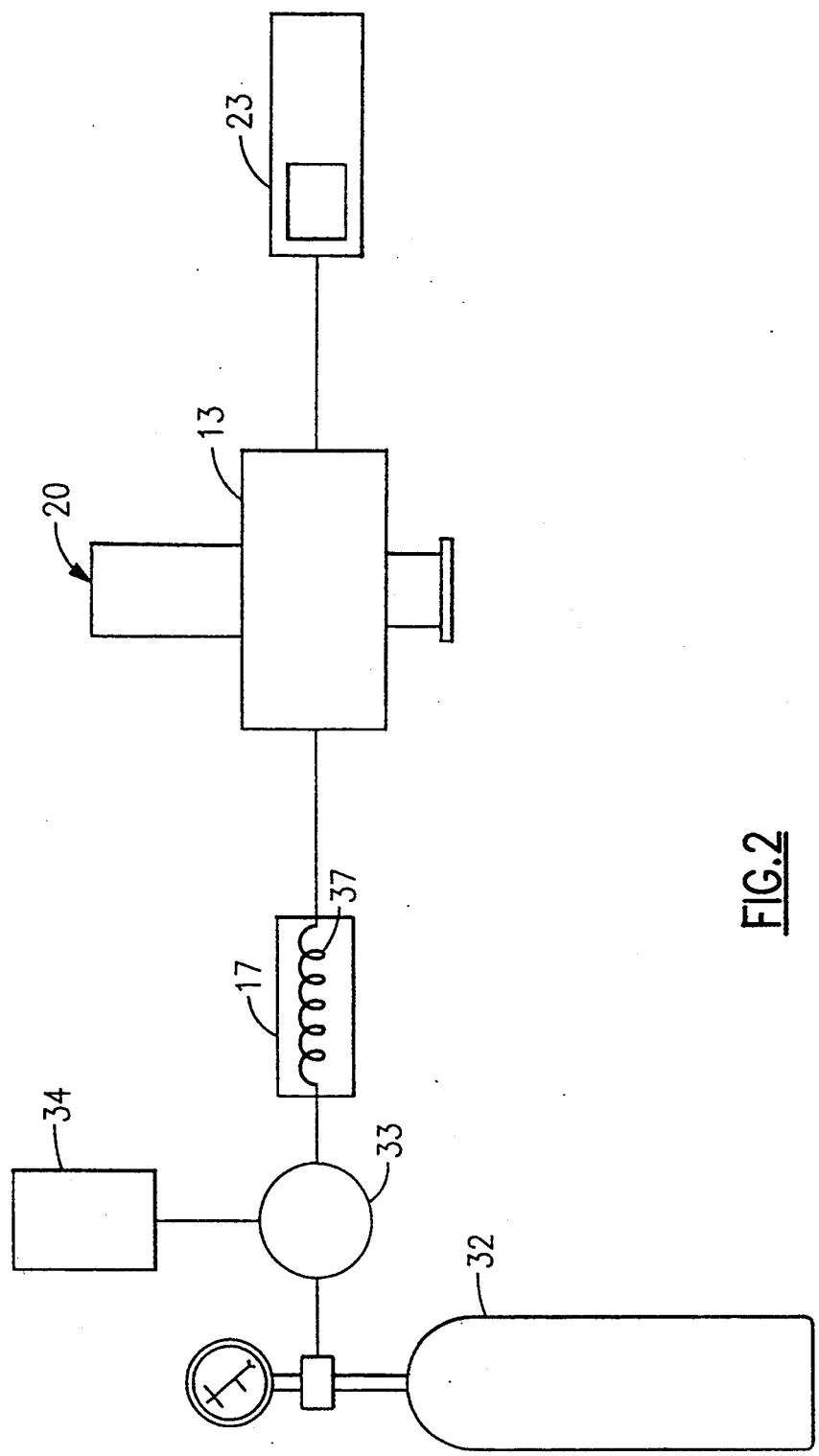
FIG. 2 is a schematic representation of the component parts contained within the portable analytical module of the present system.

With further reference to FIG. 2, there is shown in further detail analytical components contained in the analytical module. These include a supply tank 32 for storing a quantity of carrier gas under pressure. The tank is connected to a mixing valve 33 which is also connected to a sample inlet 34 for capturing a sample to be analyzed. The sample is transported by the carrier gas through the sampling tube of the gas chromatograph unit and delivered into the vacuum chamber 13 housing the mass spectrometer. The interior surface of the sampling tube is coated with a stationary phase that functions to separate the component parts from the moving phase. Depending upon the characteristics of the particular components found in the gas being analyzed, components are introduced as a series of pulses into the vacuum chamber where each pulse sample is ionized and passed through the mass spectrometer for analysis. The output of the mass spectrometer is applied to the main control unit where the data is stored in memory.

Figure 4:
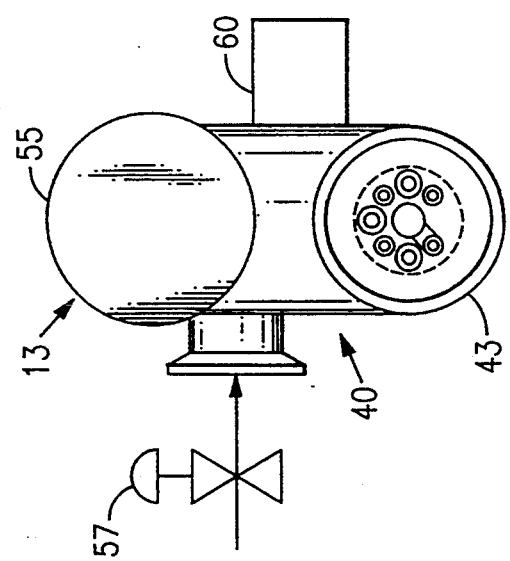
FIG. 4 is an end view of the mass spectrometer illustrated in FIG. 3.
Figure 5:
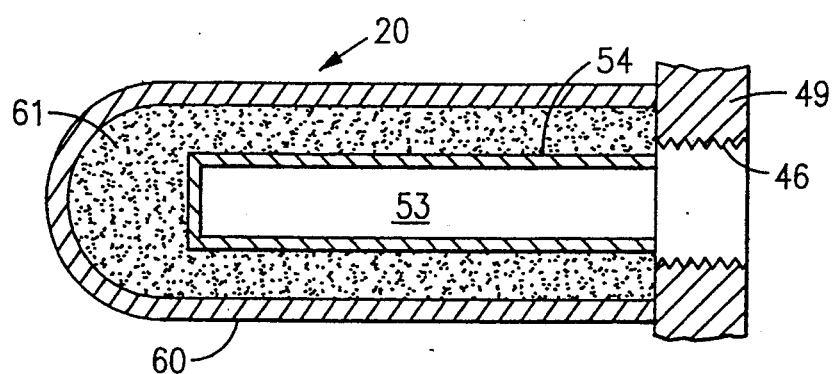
FIG.5 is an enlarged side view of the sorption pump employed in the present system.

The vacuum chamber containing the mass spectrometer 15 and the sorption pump 20 is shown in greater detail in FIGS. 3-5. The chamber includes a sealed housing 40 in which the mass spectrometer is mounted adjacent to the bottom wall 41. The electrical connections for the instrument ionization section 42 pass out of the chamber through lower left hand flange 43 and are coupled to the main control unit 23 by suitable leads (not shown). The detector section 44 of the instrument passes out of the housing via the opposing flange 47 and is similarly connected to the main control unit via suitable leads. The sorption pump 20 is mounted in the top section of the housing. The base 49 of the pump is provided with a female thread 46 (FIG. 5) which mates with a threaded male member 50 mounted on the vertical side wall 51 of the housing. A heating element 53 is passed into the vacuum chamber through the male member and is housed with a hollow cylindric core 54 of the pump (FIG. 5). The heater element is electrically connected to the heater control unit 52. The heater unit, in turn, is connected via leads 56—56 to the main control unit of the module which is programmed to regulate the heater operation in response to the demands placed on the system.

The sorption pump can be removed from the vacuum chamber by removing flange cover 55 and unthreading the pump from the male member.

The vacuum chamber is furnished with an automated valve 57 that permits the chamber to be opened to the high vacuum pump 28 when the two modules are removably attached to one another. As noted, the high vacuum pump is employed to initially pump down the vacuum chamber when the modules are attached. When the modules are separated, the automated valve is closed and the sorption pump takes over to maintain the vacuum chamber at the desired vacuum pressure.

The getter pump 20 includes the previously noted base 49 to which is bonded an outer housing 60 formed of a diffusion material that acts as a delay barrier in regard to gas molecules contained in the vacuum chamber. The diffusion material may be glass, plastic, ceramic, metal or any other similar type material used in the filtration art for this purpose. The area between the housing and the central core 54 is packed with a particulate getter material 61. Preferably the getter material is a non-evaporable material of the type known and used in the getter art.

Figure 6:
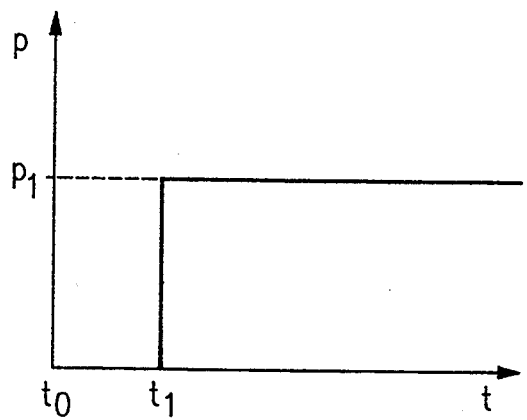
FIGS. 6–10 are graphic representations showing various characteristics of the sorption pump plotted against time.
Figure 7:
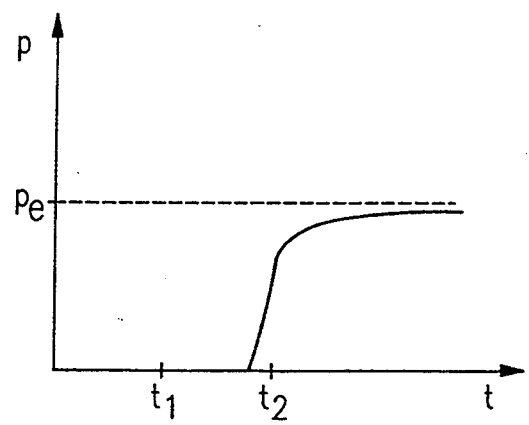

In the absence of a sampling pulse the partial pressure of a component in the chamber and within the sorptive housing are at some equal value $p_0$. Upon the introduction of a sample pulse at time $t_1$, the partial pressure at the entrance to the pump housing will increase to some higher value $P_1$. This is depicted graphically in FIG. 6 as a step function. FIG. 7 depicts the development of pressure inside the pump housing behind the diffusion barrier. During the diffusion period, the housing pressure $p_o$ remains at reference level, however, at time $t_2$ the sample gas molecules have crossed the barrier and the pressure in the housing rapidly rises and asymptotically approaches some equilibrium value $p_e$. The equilibrium value is slightly lower than the initial inlet pressure depending, among other things, on the barrier material, the getter material, and the sorption speed of the material.

Figure 8:
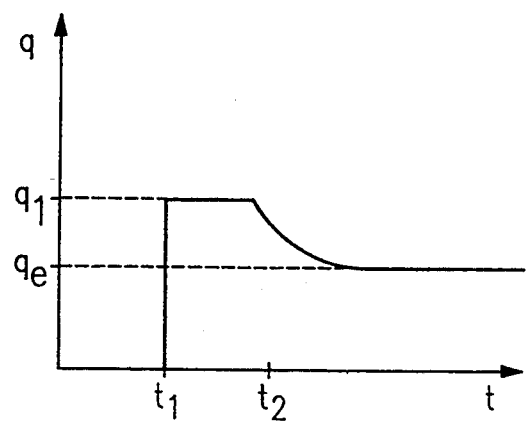
Figure 9:
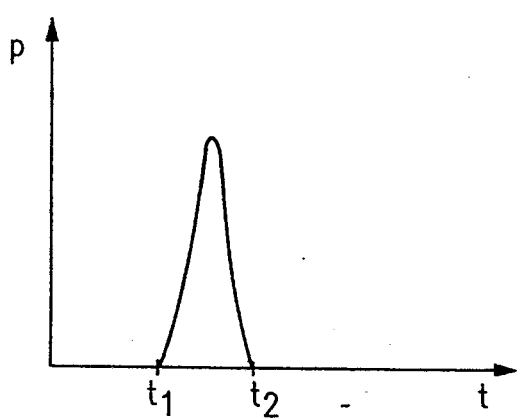
Figure 10:
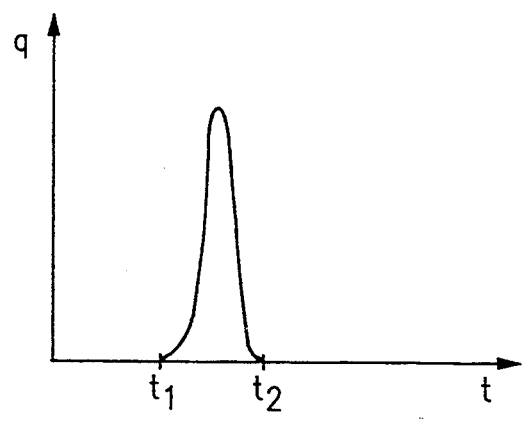

The gas flow through the inlet region of the pump is shown plotted against time in FIG. 8. Between the times $t_1$ and $t_2$, the pressure gradient over the diffusion system is at a maximum value and the gas flow $q_i$ is at a constant maximum value. As the gas molecules are captured by the getter materials, the pressure within the pump housing increases and the flow through the inlet decreases to some lesser equilibrium value $q_e$. The equilibrium value is dependent upon the sorption speed of the getter material, however it, has no influence on the initial flow $q_i$. The pumping speed of pump between times $t_1$ and $t_2$ is, therefore, constant and provides a window during which time accurate measurements of the partial pressure of the gas can be made within the vacuum chamber. Typically, the pressure at the housing inlet will not follow a step function, but rather an impulse function between times $t_1$ and $t_2$. This is shown graphically in FIG. 9. The gas flow into the housing over the diffusion barrier will also follow the pressure curve during this period as depicted in FIG. 10.

Figure 11:
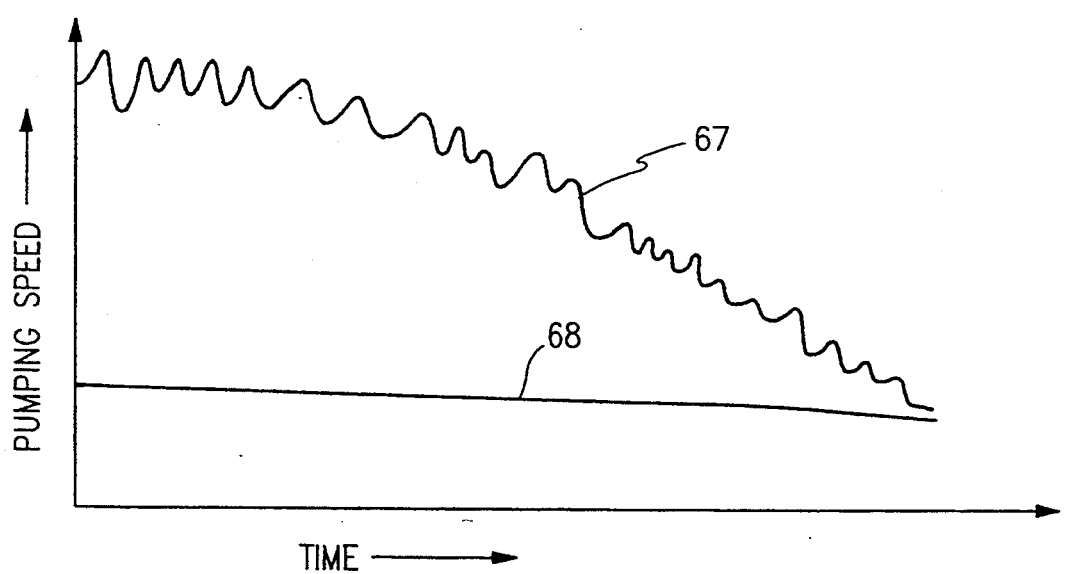
FIG. 11 is a graphic representation of the pump speed of the sorption pump with respect to time.

Turning now to FIG. 11, there is shown a graphic representation comparing the pumping speed curve 67 of a typical sorption pump with characteristic curve 68 of the present sorption pump containing a diffusion barrier. As can be seen, the pumping speed of the prior art devices falls off rather dramatically as the getter material becomes saturated. In addition, the curve contains a continuous series of spikes which make the pump unsuitable for use in vacuum chamber applications involving gas analyzing. Curve 68 represents the pumping speed characteristics of the present pump. The barrier functions to eliminate spikes and provide smooth, relatively constant pumping speed. This, coupled with the pump's repeatable behavior in response to rapid changes in the gas composition regardless of the getter condition, makes the pump ideally suited for use in a portable analytical module of the type herein described.

The sorption pump of the present invention can also be regenerated without having to be removed from the vacuum chamber. For example, where the carrier gas is hydrogen and the getter material is non-evaporable, the carrier gas captured by the getter material can be driven from the material by raising the temperature of the material using the heating element. This can be done while the analytical module is attached to the service module and the high vacuum pump is in operation. The high vacuum pump at this time serves both to pump down the vacuum chamber and to purge the released carrier gas from the system thus regenerating the sorption pump.

Because the sorption pump is incapable of pumping noble gases, a very small ion getter pump 60 (FIG. 4) is included in the analytical module to remove the residual noble gas in the vacuum chamber and to act as a pressure transducer in the system.

While this invention has been explained with reference to the structure disclosed herein, it is not confined to the details set forth and this invention is intended to cover any modifications and changes as may come within the scope of the following claims:

What is claimed is:

1. In a gas analyzing system that includes
   a vacuum chamber,
   a mass spectrometer mounted in said vacuum chamber,
   a sampling means for introducing a gas sample into said chamber,
   a sorption pump connected to the vacuum chamber, said sorption pump containing a quantity of getter material and a diffusion barrier positioned between the getter material and the interior of the chamber so that the getter material pulls gas out of the vacuum chamber at a constant rate for a given period of time during which accurate gas measurement within the vacuum chamber can be accomplished.

2. The gas analyzing system of claim 1 that further includes a high vacuum pump releasably connected to the vacuum chamber for assisting in the pumping of the system.

3. The gas analyzing system of claim 2 that further includes detachable means for removably connecting said high vacuum pump to said vacuum chamber.

4. The gas analyzing system of claim 1 wherein said sampling means further includes a gas chromatographic unit for providing sample pulses to the vacuum chamber.

5. The gas analyzing system of claim 4 that further includes supply means for delivering a non-noble carrier gas to said gas chromatographic unit.

6. The gas analyzing system of claim 5 wherein said getter material is a non-evaporable material.

7. The gas analyzing system of claim 3 wherein said sampling means further includes a gas chromatography unit and a supply means for delivering a hydrogen carrier gas to the chromatography unit.

8. The gas analyzing system of claim 7 wherein said getter material is a non-evaporating material and further includes regenerating means for releasing hydrogen gas captured by said non-evaporating getter material when the high vacuum pump is attached to the vacuum chamber whereby said released gas is removed by the high vacuum pump from the system.

9. The gas analyzing system of claim 1 wherein said sorption pump further includes a housing formed of a diffusion barrier material and a non-evaporable getter material contained within said housing.

10. The gas analyzing system of claim 9 wherein said sorption pump further includes a mounting flange for removably attaching said sorption pump to the vacuum chamber.

11. The gas analyzing system of claim 10 wherein said sorption pump further includes a heater means for raising the temperature of the non-evaporating getter material.

12. A gas analyzing system that includes:
   a portable analytical module containing a gas sampling means connected to a vacuum chamber containing a mass spectrometer and a sorption pump operatively connected to the vacuum chamber which contains a non-evaporable getter material and a diffusion barrier positioned between the getter material and the vacuum chamber whereby sample gas is pulled out of the chamber at a constant rate for a given period of time for maintaining the chamber at a high vacuum, control means containing a microprocessor for regulating the activity of the module components and memory for storing sample data from the mass spectrometer, and battery means for powering said analytical module, and
   a service module removably attachable to the analytical module containing a high vacuum pump for pumping down said vacuum chamber, charging means for recharging said battery means and data acquisition means for recovering data from said memory means.

13. The gas analyzing system of claim 12 wherein said sampling means includes a gas chromatography unit for delivering a series of gas sample pulses to the vacuum chamber.

14. The gas analyzing system of claim 13 that further includes a supply means for providing a carrier gas to the gas chromatographic unit and sample inlet means for introducing a sample gas into said carrier gas.

15. The gas analyzing system of claim 14 wherein the carrier gas is hydrogen and which further includes regenerating means for releasing hydrogen gas captured by said getter material when the analytical module is attached to the service module whereby said released gas is removed by the high vacuum pump from the system.

16. The gas analyzing system of claim 12 wherein said sorption pump further includes a housing formed of a diffusion material and a quantity of non-evaporable getter material stored within the housing whereby a finite period of time is required for gas in the vacuum chamber to cross the diffusion barrier.

17. The gas analyzing system of claim 16 wherein the getter material is in the form of particulate granules.

18. The gas analyzing system of claim 16 wherein the getter material is in the form of compressed pellets.

19. The gas analyzing system of claim 16 wherein said housing is mounted on a flange having threaded means for removably securing the sorption pump to the vacuum chamber.

20. The gas analyzing system of claim 16 that further includes a heater means for raising the temperature of the getter material.

21. The gas analyzing system of claim 12 that further includes an ion getter pump for removing residual noble gasses from the analytical module.

* * * * *